(12) United States Patent
Germano

(10) Patent No.: US 6,255,291 B1
(45) Date of Patent: *Jul. 3, 2001

(54) COMPOSITION AND METHOD FOR TREATING CANCER AND IMMUNOLOGICAL DISORDERS RESULTING IN CHRONIC CONDITIONS

(75) Inventor: Yveta Germano, Elmsford, NY (US)

(73) Assignee: Peregrine Pharmaceuticals, Inc., Gainesville, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/031,999

(22) Filed: Feb. 27, 1998

Related U.S. Application Data

(60) Provisional application No. 60/039,288, filed on Mar. 4, 1997.

(51) Int. Cl.$^7$ .................................................. A01N 43/04
(52) U.S. Cl. .................. 514/46; 514/2; 514/25; 514/45; 514/47; 514/54; 546/348; 549/315
(58) Field of Search ................................. 514/2, 25, 45, 514/46, 47, 54; 549/315; 546/348

(56) References Cited

U.S. PATENT DOCUMENTS

| 5,118,673 | * | 6/1992 | Carpenter et al. ...................... 514/54 |
| 5,672,590 | * | 9/1997 | Kufudaki ............................... 514/53 |
| 5,747,474 | * | 5/1998 | Ojo-Amaize et al. .................. 514/46 |

FOREIGN PATENT DOCUMENTS

9726893 * 7/1997 (WO) .

* cited by examiner

*Primary Examiner*—James O. Wilson
(74) *Attorney, Agent, or Firm*—Bruce F. Jacobs

(57) ABSTRACT

A composition containing alph-alanine, adenosine compound and a glucan. Methods for treating cancer and immunological disorders with said composition.

28 Claims, 2 Drawing Sheets

COMPOSITION AND METHOD FOR TREATING CANCER AND IMMUNOLOGICAL DISORDERS RESULTING IN CHRONIC CONDITIONS

This application claims the benefit of U.S. Provisional Application No. 08/039,288 filing date Mar. 4, 1997.

FIELD OF THE INVENTION

The present invention is directed to a composition for treating early stages of various forms of malignancies, particularly melanoma and lung cancer, in mammals. In more advanced stages of malignancies, such as those involving larger tumors and/or metastases, the composition is designed to be used as an adjunct and adjuvant therapy with other procedures such as surgery, chemotherapy, radiation therapy, antibody therapy, and others. The composition can also be used for treating various immunological disorders resulting in chronic conditions, especially those leading to inflammatory events, such as rheumatoid arthritis, cystic fibrosis, psoriasis, and pleural disease.

BACKGROUND OF THE INVENTION

Cancer afflicts many individuals each year. Melanoma tumors, for instance, originate from melanocytes, pigment cells that are normally present in the epidermis and sometimes in the dermis. Melanoma affects about 28,000 individuals yearly in the United States and kills about 5,800 of these individuals. Melanoma incidence has increased dramatically (700% in the last 40 years). If the incidence continues to increase at the present rate, risk of melanoma will approximate about 1 percent within a decade lifetime.

There are various types of malignant neoplasm affecting the lung, such as adenosquamous carcinoma, small cell (oat cell) carcinoma, large cell carcinoma, and others. These malignancies can affect various parts of the lung and can be classified into several types depending on the site, such as alveoral carcinoma, bronchiolar carcinoma, bronchogenic carcinoma, and others. In general, malignancies of the lung account forthe highest incidence of cancer in the United States. At the same time, the various forms of lung cancer account for the highest death rates.

Immune system is involved in a pathologic process called inflammation, which is a complex of cytologic and chemical reactions occurring in the tissues and blood vessels in response to an injury or abnormal stimulation. Inflammation is usually a relatively quick response with a rapid onset. Sometimes, however, the inflammatory response is insufficient, allowing the persistence of the injuring agent or its products in the tissues, resulting in chronic inflammation. Some cell-mediated inflammatory mechanisms may be directed towards autoantigens causing chronic tissue-damaging inflammation. Types of such chronic inflammations include rheumatoid arthritis, psoriasis, Chrohn's disease, cystic fibrosis, and others.

Immunomodulating compositions have been designed to treat various immunodeficiencies and autoimmunological disorders. Ongoing research continues to evaluate whether these compositions may be useful in treating one or more malignant diseases.

Greek Patent Specification No. 72,440 discloses an immunomodulating composition containing a mixture of D-ribose, DL-alpha alanine, nicotinic acid and ascorbic acid. The composition asserted to have a pronounced immunomodulating activity and to be able to rebuild the metabolic equilibrium and strengthen the immunity of an affected mammal.

PCT application CZ94/00015, filed Jul. 12, 1994, and U.S. Ser. No. 08/564,328 (the U.S. equivalent to the PCT application) disclose an improvement upon the Greek patent and incorporate 2-deoxy-D-ribose, thiamin, and glutamic acid amide therein. The resulting improved composition has been found useful in immunomodulating and adjuvant therapy in combination with a metabolic stressor.

Co-pending U.S. patent application Ser. No. 08/787,209, discloses a composition of a ribose compound, L-beta-alanine, ascorbic acid, and nicotinic acid, and adenosine-5'-monophosphate disodium salt.

It has now been unexpectedly discovered that adding an adenosine compound and a glucan to the alpha-alanine-containing compositions of PCT application CZ94/00015 significantly enhances a mammal's resistance to cancer, particularly melanoma and lung cancer, and significantly enhances the mammal's immunological response.

It is an object of this invention to make a composition which will enhance a mammal's resistance to cancer and prolong that mammal's life.

It is a further object of this invention to produce a composition that inhibits the growth of a cancer tumor.

It is a further object of this invention to treat a mammal with cancer by introducing the composition into the bloodstream of the mammal.

It is a further object of this invention to produce a composition that enhances the immunological response of the organism.

It is a further object of this invention to stimulate a mammal's immune system response by introducing the composition orally into the stomach of the mammal.

These and still further objects will be apparent from the following description of this invention.

SUMMARY OF THE INVENTION

The present invention is directed to a composition containing alpha-alanine. The composition preferably comprises alpha-alanine, an adenosine compound, a ribose compound, ascorbic acid, and nicotinic acid. More preferably the composition comprises alpha-alanine, an adenosine compound, ribose compounds, ascorbic acid, nicotinic acid, and a glucan. The composition may be prepared in a soluble form in a sodium chloride (saline solution) solution or in a particulate form by blending all of the compounds into a dry, homogenous mixture. The present invention also includes a method for treating cancer tumors in mammals by introducing the composition into the bloodstream of the mammal. The present invention further includes a method for curing cancer involving the steps of (i) introducing a composition of this invention into a mammal and (ii) removing a cancer tumor from a mammal. The present invention also includes a method for stimulating an immune response in mammals by introducing the composition orally into the stomach of the mammal.

DESCRIPTION OF THE PREFERRED EMBODIMENTS

Figure 1:
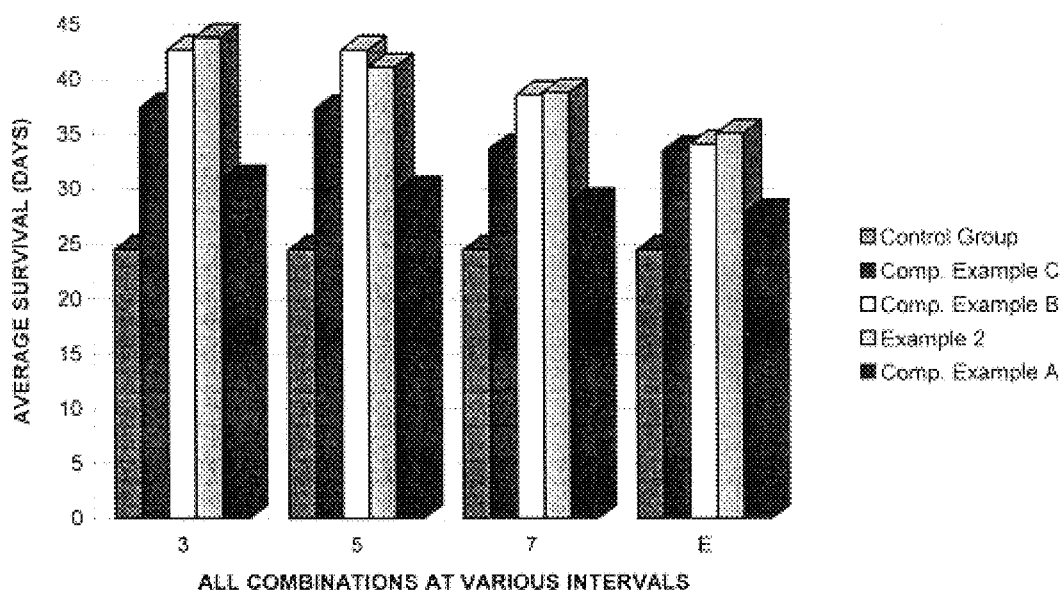
FIG. 1 is a graph showing the average survival period at 50 days after tumor inducement of melanoma-inflicted mice treated with a composition of this invention at 3, 5, 7 and 10 days after tumor inducement (and untreated melanoma-inflicted mice).

The present invention is directed to a composition containing alpha-alanine and an adenosine compound. Preferably, the composition comprises alpha-alanine, an adenosine compound, a ribose compound, ascorbic acid, and nicotinic acid. The present invention is also directed to a method for treating cancer tumors in mammals with the composition. Animal studies indicate that the composition prolongs the life of a mammal with a melanoma significantly, e.g. by at least about 25% and preferably by as much as 100%, as compared to a mammal with melanoma that does not receive any treatment. Animal studies also indicate that the composition inhibits the growth of tumors. Animal studies also indicate that the composition has a significant effect in the prevention of metastasis of lung carcinoma. The studies also indicate that the composition has a high therapeutic effect on the lung carcinoma, resulting in as much as a 55% cure rate of the animals.

The present invention is further directed to a composition containing alpha-alanine, an adenosine compound, and a glucan. Preferably, the composition comprises alpha-alanine, an adenosine compound, ribose compounds, ascorbic acid, nicotinic acid, and a glucan. The present invention is also directed to the method for enhancing a mammal's immune system response measured by Colony Forming Units (CFU's), production of Interleukin-2, cell proliferation with mitogens such as Concanavalin A, PHA, and LPS. All of these immunological markers play an important role in the treatment of cancer, as well as various immunological disorders including chronic inflammatory conditions.

The alpha-alanine is generally present at an amount of at least about 1 wt %, preferably at least about 5 wt %, and more preferably at least about 8 wt %, based on the total dry weight of the composition. Suitable amounts ordinarily range from about 1 to about 45 wt %, more preferably from about 5 to about 25 wt %, and more preferably from about 8 and about 15 wt %, based on the total dry weight of the composition. Other ranges within the ranges expressly disclosed above may also be suitable.

The adenosine compound is adenosine or an adenosine derivative and is advantageous to the metabolic activity of cells. The adenosine compound will ordinarily be an adenosine triphosphate-forming compound such as a nicotinic acid derivative or precursor thereof. Suitable such nicotinic acid derivatives include nicotinamide adenine dinucleotide, hydronicotinamide adenine dinucleotide, nicotinamide adenine dinucleotide phosphate, beta-nicotinamide adenine dinucleotide monohydrate, beta-nicotinamide adenine dinucleotide dihydrate, beta-nicotinamide adenine dinucleotide phosphate disodium salt, beta-nicotinamide adenine dinucleotide phosphate sodium salt, beta-nicotinamide adenine dinucleotide phosphoric acid, beta-nicotinamide mononucleotide. Adenosine monophosphate may be used as a precursor to nicotinamide adenine dinucleotide. Other structurally or functionally equivalent adenosine compounds may also be suitable.

For instance, examples of some other adenosine compounds include, but are not limited to, adenosine-5'-monophosphate disodium salt, adenosine-3'5'-cyclophosphate sodium salt monohydrate, adenosine-3'5'-cyclophosphoric acid, adenosine deaminase, adenosine-5' diphosphate disodium salt, adenosine-5'-diphosphate monopotassium salt dihydrate, adenosine-5'-diphosphoric acid, adenosine-5'-[β,γ-imido] triphosphate tetralithium salt dihydrate, adenosine-5'-[α,γ-methylene] diphosphoric acid, adenosine-5'-[α, β-methylene] triphosphate tetralithium salt, adenosine-5'-[β,γ-methylene] triphosphate tetralithium salt, adenosine-5'-monophosphoramidate sodium salt, adenosine-3'-monophosphoric acid, adenosine-3'-(+2)-monophosphoric acid monohydrate, adenosine-5'-monophosphoric acid monohydrate, adenosine-3'-phosphate-5'-phosphosulfate tetralithium salt tetrahydrate, adenosine-5'-[β-thio] diphosphate trilithium salt, adenosine-5'-[α-thio] monophosphate dilithium salt, adenosine-5'-[γ-thio] triphosphate tetralithium salt, adenosine-5'-triphosphatase, adenosine-5'-triphosphate bis (TRIS) salt dihydrate, adenosine-5'-triphosphate dipotassium salt dihydrate, adenosine-5'-triphosphate disodium salt hydrate, adenosine-5'-triphosphate immobilized on agarose 4B, adenosine-5'-triphosphate magnesium salt hydrate, and adenosine-5'-triphosphate $P^3$-[1-(2-nitrophenyl) ethylester] disodium salt.

The adenosine compound is generally present at an amount of at least 1 wt %, preferably at least about 5 wt %, and more preferably at least about 8 wt %, based on the total dry weight of the composition. Suitable amounts ordinarily range from about 1 to about 50 wt %, preferably from about 8 to about 20 wt %, and more preferably from about 5 to about 25 wt %, based on the total dry weight of the composition. Other ranges within the ranges expressly disclosed above may also be suitable. The alpha-alanine and the other ingredients of the composition are known materials that can be obtained from manufacturers such as Sigma Aldrich and Merck.

Suitable ribose compounds for use herein include, but are not limited to, ribose, deoxyribose (2-deoxy-D-ribose), other ribose derivatives, and mixtures thereof. Specific examples of suitable ribose compounds include, but are not limited to, D-ribose, D-ri-bose 1-phosphate cyclohexylamine salt, D-ribose 5-phosphate barium salt hexahydrate, D-ribose 5-phosphate disodium salt dihydrate, and 2-deoxy-alpha-D-ribose 1 phosphate bis (cyclohexylamine) salt. Other structurally or functionally equivalent ribose compounds may be suitable.

The ribose compound is ordinarily present at an amount of at least about 20 wt %, preferably at least about 35 wt %, and more preferably at least about 40 wt %, based on the total dry weight of the composition. Suitable amounts ordinarily range from about 20 to about 60 wt %, more preferably from about 35 to about 50 wt %, and more preferably from about 38 and about 46 wt %, based on the total dry weight of the composition. Other ranges within the ranges expressly disclosed above may also be suitable.

Ascorbic acid is ordinarily present at an amount of at least about 10 wt %, preferably at least about 15 wt %, and more preferably at least about 20 wt %, based on the total dry weight of the composition. Suitable amounts ordinarily range from about 10 to about 30 wt %, preferably from about 15 to about 28 wt %, and more preferably from about 20 to about 23 wt %, based on the total dry weight of the composition. Other ranges within the ranges expressly disclosed above may also be suitable.

Nicotinic acid is generally present at an amount of at least about 1 wt %, preferably at least about 3 wt %, and more preferably at least about 6 wt %, based on the total dry weight of the composition. Suitable amounts ordinarily range from about 1 to about 45 wt %, more preferably from about 5 to about 25 wt %, and more preferably from about 6 to about 15 wt %, based on the total dry weight of the composition. Other ranges within the ranges expressly disclosed above may also be suitable.

Glucose is the main source of energy for metabolism. Higher organisms protect themselves from the possible lack of this energy by polymerizing the excess glucose into high molecular glucans from which the glucose can easily be obtained when necessary for the organism.

Glucans, however, can also be found in many microorganisms. Depending on which microorganisms the glucans are isolated from, there can be many types of glucans. Some of the most common yeast species from which glucans can be isolated include Candida, Saccharomyces, Cryptococcus, and others. Several types of glucans, for example β-1,3-glucan, have been isolated from the strains of *Saccharomyces cerevisiae*. Other fungi, for example *Sclerotinia sclerotiorum*, have also been used to isolate glucans. In general, several glucans have been scientifically investigated and found to be effective in the activation of natural killer cells.

Suitable glucans for use herein include, but are not limited to, β-1,3-glucan, β-1,3-polyglucose, β-1,3-glucan glucopyranose, or β-1,3-D-polyglucose derivatives. The glucan compound is ordinarily present at an amount of at least about 5 wt %, preferably at least about 10 wt %, and more preferably at least about 25 wt %, based on the total dry weight of the composition. Suitable amounts ordinarily range from about 5 to 99 wt %, preferably from about 10 to about 85 wt %, and more preferably from about 25 to about 65 wt %, based on the total dry weight of the composition. Other ranges within the ranges expressly disclosed above may also be suitable.

Furthermore, the composition may contain stabilizers, e.g. $NaHCO_3$, to increase the pH of the composition.

The composition may be prepared by compounding the alpha-alanine, adenosine compound, ribose compound, ascorbic acid, and nicotinic acid in a suitable delivery means, e.g. a sodium chloride (saline) solution. The ingredients may be mixed conventionally, i.e. by stirring each ingredient separately into the sodium chloride solution, until a substantially homogenous mixture is obtained. For instance, the ribose compound (or mixtures of ribose compounds) may be first added to a sodium chloride solution. Then, ascorbic acid is added until it fully dissolves. Then, D,L-alpha-alanine is added until it dissolves. Nicotinic acid may then be added, and finally, the adenosine compound is added. The mixture may then be filtered through the membrane filter and bottled in sterile ampoules (or small sterile bottles used for injections). The mixing time required to form the homogenous mixture depends on factors such as the temperature, the degree of mixing, and the like. The mixing temperature is preferably about room temperature, but it is not critical provided that none of the ingredients are harmed by exposure to heat.

Preferably, the composition is prepared by forming two separate pre-mixtures of specific ingredients and then combining the two pre-mixtures. For instance, the composition may be prepared by a method that involves (i) forming a first pre-mixture of the ascorbic acid, ribose compound, water, and sodium chloride; (ii) forming a second pre-mixture of alpha-alanine, adenosine compound, nicotinic acid, water, and sodium chloride; and (iii) combining the two pre-mixtures prior to use. The blended composition has been found to have a storage stability of up to about 6 months. Therefore, it is preferable that the two pre-mixtures be kept separate until shortly prior to administration, i.e. within a few months. Although not currently recommended, it may be possible to administer the two pre-mixtures sequentially. When a glucan is present, a soluble form must be used in order to prepare a solution. If glucan is used, it is preferably added to the second pre-mixture.

The composition may also be prepared in a dry form by carefully blending all ribose compounds and adding the individual components one at a time after a complete homogenous dry substance is achieved. This dry form can utilize various insoluble forms of glucans, more preferably β-1,3-glucan.

The composition is preferably administered to a mammal intravenously, but may also be administered in other ways, e.g. capsules, tablets, powders, drinking liquids, suppositories, sprays, time-release media, and the like. A preferable delivery means for intravenous administration of the composition is a sodium chloride (saline) solution. The composition may also be administered intratumorally, intraperitonially, topically, subdermally, orally, or by any other suitable means.

The mechanism by which the composition of the present invention prolongs the lives of cancer-inflicted mammals has not been determined, and Applicant does not wish to be bound by any theory. However, evidence suggests that the composition stimulates (i) endogenous immune reactions including the mammal's ability to synthesize cytokines and (ii) primary and secondary immune responses.

The invention is illustrated in the following nonlimiting examples. All parts and percents are by total weight of the dry composition unless otherwise specified.

EXAMPLE 1

A composition of this invention was prepared as follows. A first pre-mixture was formed using a mixer equipped with a stirrer and a source of nitrogen. The mixer was filled with 5 ml water and sterile nitrogen was bubbled through the water for about 20 minutes. During the nitrogen bubbling, 300 mg of 2-deoxy-D-ribose was added and mixed into the water. Then, 45 mg sodium chloride and 150 mg ascorbic acid were dissolved in the water. No direct sunlight was allowed to contact the mixture. The resulting first premixture solution was sterilized by passing it through a membrane filter. The solution was placed into a 5 cc vial under nitrogen in an aseptic environment.

A second pre-mixture was prepared by mixing 50 mg nicotinic acid, 5 ml water, 45 mg sodium chloride, 80 mg of L-alpha-alanine, and 80 mg of adenosine-5'-monophosphate disodium salt in the same manner as the first pre-mixture. The second pre-mixture was also filtered through a membrane filter and the solution was placed in a 5 cc vial and sealed. The sealed vial was sterilized in an autoclave for about 20 minutes at 120° C.

EXAMPLE 2

To evaluate the effectiveness of the composition of Example 1 in prolonging the life of mammals having melanoma, 50 inbred female mice weighing about 18–20 grams each were divided into one experimental group of 40 mice and a control group of 10 mice. The group of 40 mammals was divided into four subgroups (A, B, C, D) with 10 mice in each subgroup. To induce melanoma tumors in the mice, all 50 mice were subcutaneously administered with about two million tumor cells of melanoma B16.

Thereafter, about 0.05 ml of the treatment composition prepared as in Example 1 and administered twice (once intravenously in the morning and once intraperitonially in the afternoon). The first and the second pre-mixtures were mixed together to form the treatment composition from about 1 to 6 hours prior to actual use. In subgroup A, the treatment composition was administered 3 days after tumor inducement. In subgroup B, the treatment composition was administered 5 days after tumor inducement. In subgroup C, the treatment composition was administered 7 days after tumor inducement. In subgroup D, the treatment composition was administered 10 days after tumor inducement. In all subgroups, the primary melanoma tumor was surgically removed 10 days after tumor inducement (only metatastic tumors were left in). In subgroup D, the primary melanoma tumor was surgically removed prior to administration of the treatment composition.

The primary melanoma tumor was also surgically removed 10 days after tumor inducement in all mice in the control group. The mice in the control group were administered a physiological saline solution daily from the 10th day after tumor inducement until the last mouse had died, 32 days the melanoma tumors had been induced.

Mice Survival

Table 1 identifies the number of days before the last of the mice in each subgroup and control group died.

TABLE 1

| SUBGROUP | MICE SURVIVAL |
|---|---|
| A | more than 100 days |
| B | more than 100 days |
| C | more than 100 days |
| D | 88 |
| Control Group | 32 |

As Table 1 indicates, the treatment composition administered at 3, 5, 7, and 10 days after melanoma tumor inducement substantially prolonged the life of the mammals. 12 mice survived more than 100 days.

Average Survival Periods

The average number of days the mice in all subgroups survived after tumor inducement were calculated on the 50th and 100th day after tumor inducement. The results are shown in Table 2.

TABLE 2

|  | A | B | C | D |
|---|---|---|---|---|
| 50 days | 43.8 | 41.1 | 38.8 | 35.1 |
| 100 days | 69.6 | 61.1 | 56 | 38.9 |
| Control | 24.5 | 24.5 | 24.5 | 24.5 |

Table 2 indicates that the composition of the present invention was highly effective in all subgroups.

COMPARATIVE EXAMPLE A

In this Example, the procedure of Example 2 was repeated except that the composition was made from 80 mg D,L-alpha alanine, 150 mg D-ribose, 150 mg 2-deoxy-D-ribose, 150 mg ascorbic acid, 50 mg nicotinic acid, 10 ml water and 90 ml sodium chloride, i.e. a composition disclosed in PCT application CZ94/00015 and U.S. Ser. No. 08/564,328.

Mice Survival

Table 3 identifies the mice survival, i.e. the number of days before the last of the mammals in the experimental subgroup and the control group dies.

TABLE 3

| SUBGROUP | MICE SURVIVAL |
|---|---|
| A | 51 days |
| B | 50 days |
| C | 41 days |
| D | 35 days |
| Control | 32 days |

The mice survival, although superior to the control group, was significantly less in all subgroups as compared with the mice survival of Example 2.

Average Survival Periods

The average survival periods of the mice in each subgroup and control group were calculated on the 50th and 100th day after tumor inducement. Table 4 shows the average survival period (in days) of the mice in subgroups A, B, C and D.

TABLE 4

|  | A | B | C | D |
|---|---|---|---|---|
| 50 days | 30.9 | 29.9 | 28.8 | 27.8 |
| 100 days | 30.9 | 29.9 | 28.8 | 27.8 |
| Control | 24.5 | 24.5 | 24.5 | 24.5 |

The average survival period of the mice in this Comparative Example was significantly lower in comparison to the average survival period of the mice of Example 2.

COMPARATIVE EXAMPLE B

For comparison purposes, the procedure of Example 2 was repeated except that the composition was made with L-beta alanine instead of D,L-alpha alanine. Table 5 shows the mice survival of each subgroup.

TABLE 5

| SUBGROUP | MICE SURVIVAL |
|---|---|
| A | more than 100 days |
| B | more than 100 days |
| C | more than 100 days |
| D | 83 days |
| Control Group | 32 days |

The mice survival of subgroups A, B, and C was the same as the mice survival of subgroups A, B, and C in Example 2. The mice survival of subgroup D was somewhat less than the mice survival of subgroup D in Example 2. 8 mice survived more than 100 days.

Average Survival Periods

The average survival periods of the mice in each subgroup and control group were calculated on the 50th and 100th day after tumor inducement. The results are shown in Table 6.

TABLE 6

|  | A | B | C | D |
|---|---|---|---|---|
| 50 days | 42.7 | 42.7 | 38.6 | 34.1 |
| 100 days | 57.4 | 58.8 | 56 | 46.3 |
| Control | 24.5 | 24.5 | 24.5 | 24.5 |

The average survival period of all subgroups at 50 days was comparable to the average survival period of all subgroups at 50 days in Example 2. The average survival period of all subgroups at 100 days was significantly less (57.4 vs 69.6 days) than the average survival period at 100 days for the mice of Example 2.

COMPARATIVE EXAMPLE C

The procedure of Comparative Example B was repeated except that the composition was not made with the adenosine-5'-monophosphate disodium salt. Table 7 shows the results.

TABLE 7

| SUBGROUP | MICE SURVIVAL |
| --- | --- |
| A | more than 100 days |
| B | more than 100 days |
| C | more than 100 days |
| D | 51 days |
| Control Group | 32 days |

The mice survival of subgroups A, B, and C was the same as the mice survival of Example 2. The mice survival of subgroup D was significantly less than the mice survival of subgroup D of Example 2. 5 mice survived more than 100 days.

Average Survival Periods

The average survival periods of the mice in each subgroup and control group were calculated on the 50th and 100th day after tumor inducement. The results are shown in Table 8.

TABLE 8

|  | A | B | C | D |
| --- | --- | --- | --- | --- |
| 50 days | 37.5 | 37.3 | 33.7 | 33.5 |
| 100 days | 42.5 | 47.4 | 43.7 | 33.6 |
| Control | 24.5 | 24.5 | 24.5 | 24.5 |

Figure 2:
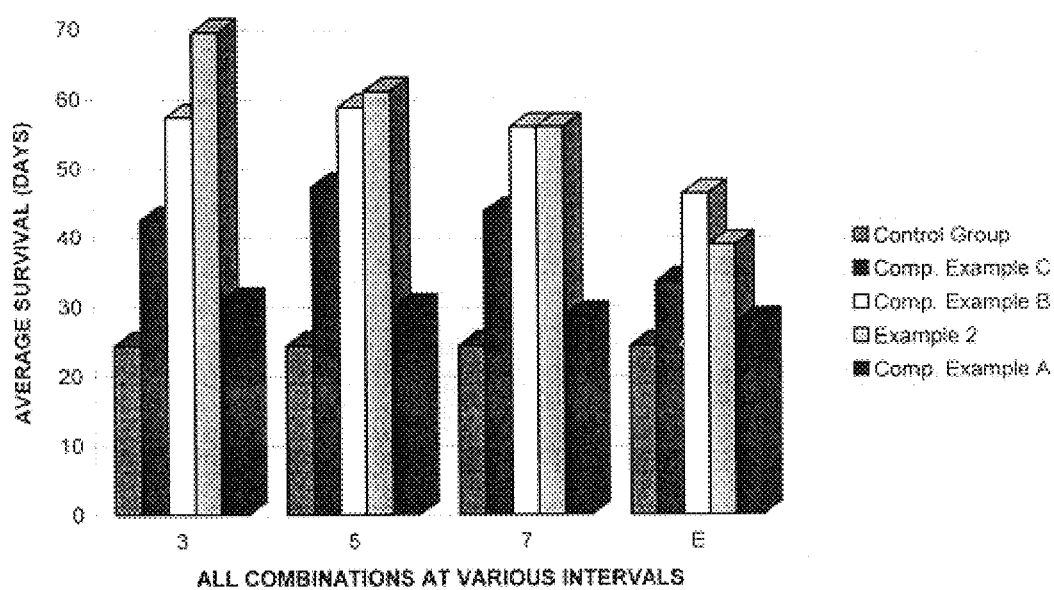
FIG. 2 is a graph showing the average survival period at 100 days after tumor inducement of melanoma-inflicted mice treated with a composition of this invention at 3, 5, 7 and 10 days after tumor inducement (and untreated melanoma-inflicted mice).

FIGS. 1 and 2 are graphs that summarize the average survival period of mice treated with the compositions of Examples 2, Comparative Example A, Comparative Example B, and Comparative Example C.

EXAMPLE 4

To evaluate the effectiveness of the composition of this invention in inhibiting the growth of the induced melanoma tumors, the procedure of Example 2 was repeated and the size of each induced tumor was measured after the tumor was removed on the 10th days after tumor inducement. Table 9 shows the diameter of the tumors in centimeters.

TABLE 9

| SUBGROUP | TUMOR SIZE |
| --- | --- |
| A | 0.41 |
| B | 0.49 |
| C | 0.55 |
| D | 0.77 |
| Control | 0.77 |

The results indicate that in subgroups A, B, and C, the composition of this invention substantially reduced the size of the tumor.

COMPARATIVE EXAMPLE D

For comparative purposes, the procedure of Example 4 was repeated except that the composition of Comparative Example B was used, i.e. the composition containing L-beta-alanine, 2-deoxy-D-ribose, sodium chloride, and ascorbic acid, nicotinic acid and adenosine-5'-monophosphate disodium salt. Table 10 shows the diameter of the tumors (in cm) removed 10 days after tumor inducement.

TABLE 10

| SUBGROUP | COMP. EXAMPLE D | EXAMPLE 4 |
| --- | --- | --- |
| A | 0.52 | 0.41 |
| B | 0.58 | 0.49 |
| C | 0.73 | 0.55 |
| D | 0.75 | 0.77 |
| Control | 0.77 | 0.77 |

As compared with the results of Example 4, the tumor size indicate that subgroups A, B, and C were significantly larger in subgroups A, B and C indicating that the composition used in Comparative Example D was inferior to the composition used in Example 4.

COMPARATIVE EXAMPLE E

For comparative purposes, the procedure of Example 4 was repeated except that the composition of Comparative Example C was used, i.e. the composition containing L-beta-alanine, 2-deoxy-D-ribose, sodium chloride, and ascorbic acid, and nicotinic acid. Table 11 shows the diameter of the tumors (in cm) 10 days after tumor inducement.

TABLE 11

| SUBGROUP | COMP. EXAMPLE E | COMP. EXAMPLE D | EXAMPLE 4 |
| --- | --- | --- | --- |
| A | 0.61 | 0.52 | 0.41 |
| B | 0.74 | 0.58 | 0.49 |
| C | 0.8 | 0.73 | 0.55 |
| D | 0.78 | 0.75 | 0.77 |
| Control | 0.77 | 0.77 | 0.77 |

The results indicate that the composition in all subgroups of Comparative Example E did not inhibit the growth of the tumors for any subgroup as compared to the compositions used in Example 4.

EXAMPLE 5

To evaluate whether the mice surviving more than 100 days since tumor inducement had tumors (the mice of Example 2, Comparative Example B, and Comparative Example C), the mice were killed 200 days after tumor inducement and their bodies were surgically opened and checked for melanoma tumors.

Table 12 indicates the number of mice surviving in Example 2, Comparative Example B, and Comparative Example C and the number of cancer-free mice in each example.

TABLE 12

| Mice | # Mice Surviving more than 100 days | # Cancer-Free Mice |
| --- | --- | --- |
| Example 2 | 12 | 12 |
| Comp. Ex B | 8 | 6 |
| Comp. Ex C | 5 | 2 |

Table 12 indicates that the composition of this invention cured cancer in 100% of the surviving mice.

What is claimed is:

1. A composition consisting essentially of about 8 to 15 wt % alpha-alanine, about 8 to 20 wt % of an adenosine compound, about 35 to 50 wt % of a ribose compound, about 15 to 28 wt % ascorbic acid, and about 6 to 15 wt % nicotinic acid.

2. The composition of claim 1, wherein the alanine is D,L-alanine.

3. The composition of claim 2, wherein the adenosine compound is selected from the group consisting of adenosine and adenosine derivatives.

4. The composition of claim 3, wherein the adenosine derivative is selected from the group consisting of an adenosine triphosphate-forming compound; nicotinamide adenine dinucleotide; hydronicotinamide adenine dinucleotide; nicotinamide adenine dinucleotide phosphate; beta-nicotinamide adenine dinucleotide monohydrate; beta-nicotinamide adenine dinucleotide dihydrate; beta-nicotinamide adenine dinucleotide phosphate disodium salt; beta-nicotinamide adenine dinucleotide phosphate sodium salt; beta-nicotinamide adenine dinucleotide phosphoric acid; beta-nicotinamide mononucleotide; and nicotinamide adenine dinucleotide.

5. The composition of claim 3, wherein the adenosine derivative is selected from the group of adenosine-5'-monophosphate disodium salt, adenosine-3'5'-cyclophosphate sodium salt monohydrate, adenosine-3'5'-cyclophosphoric acid, adenosine deaminase, adenosine-5'-diphosphate disodium salt, adenosine-5'-diphosphate monopotassium salt dihydrate, adenosine-5'-diphosphoric acid, adenosine-5'-[β,γ-imido]triphosphate tetralithium salt dihydrate, adenosine-5'-[α,β-methylene] diphosphoric acid, adenosine-5'-[α,β-methylene] triphosphate tetralithium salt, adenosine-5'-[β,γ-methylene] triphosphate tetralithium salt, adenosine-5'-monophosphoramidate sodium salt, adenosine-3'-monophosphoric acid, adenosine-3'-(+2)-monophosphoric acid monohydrate, adenosine-5'-monophosphoric acid monohydrate, adenosine-3'-phosphate-5'-phosphosulfate tetralithium salt tetrahydrate, adenosine-5'-[β-thio] diphosphate trilithium salt, adenosine-5'-[α-thio] monophosphate dilithium salt, adenosine-5'-[γ-thio] triphosphate tetralithium salt, adenosine-5'-triphosphate, adenosine-5'-triphosphate bis(TRIS)salt dihydrate, adenosine-5'-triphosphate dipotassium salt dihydrate, adenosine-5'-triphosphate disodium salt hydrate, adenosine-5'-triphosphate magnesium salt hydrate, and adenosine-5'-triphosphte $P^3$-[1-(2-nitro-phenyl)ethylester] disodium salt.

6. The composition of claim 2, wherein the adenosine compound is present at an amount ranging from about 1 to about 50 wt %, based on the total dry weight of the composition.

7. The composition of claim 2, wherein the composition further comprises a glucan.

8. The composition of claim 7, wherein the glucan is selected from the group consisting of β-1,3-glucan, β-1,3-polyglucose, β-1,3-glucan glucopyranose, and β-1,3-D-polyglucose derivatives.

9. The composition of claim 7, wherein the glucan is present in an amount ranging from about 5 to about 99 wt %, based on the dry weight of the composition.

10. The composition of claim 7, wherein the glucan is isolated from a yeast species selected from the group consisting of Candida, Saccharomyces, and Cryptococcus.

11. A composition made by combining about 8 to 15 wt % alpha-alanine, about 8 to 20 wt % of an adenosine compound, about 35 to 50 wt % of a ribose compound, about 15 to 28 wt % ascorbic acid, and about 6 to 15 wt % nicotinic acid.

12. The composition of claim 11, wherein the alanine is D,L-alanine.

13. The composition of claim 12, wherein the adenosine compound is selected from the group consisting of adenosine and adenosine derivatives.

14. The composition of claim 13, wherein the adenosine derivative is selected from the group consisting of an adenosine triphosphate-forming compound; nicotinamide adenine dinucleotide; hydronicotinamide adenine dinucleotide; nicotinamide adenine dinucleiotide phosphate; beta-nicotinamide adenine dinucleotide monohydrate; beta-nicotinamide adenine dinucleotide dihydrate; beta-nicotinamide adenine dinucleotide phosphate disodium salt; beta-nicotinamide adenine dinucleotide phosphate sodium salt; beta-nicotinamide adenine dinucleotide phosphoric acid; beta-nicotinamide mononucleotide; and nicotinamide adenine dinucleotide.

15. The composition of claim 12, wherein the adenosine derivative is selected from the group of adenosine-5'-monophosphate disodium salt, adenosine-3'5'-cyclophosphate sodium salt monohydrate, adenosine-3'5'-cyclophosphoric acid, adenosine deaminase, adenosine-5'-diphosphate disodium salt, adenosine-5'-diphosphate monopotassium salt dihydrate, adenosine-5'-diphosphoric acid, adenosine-5'-[β,γ-imido] triphosphate tetralithium salt dihydrate, adenosine-5'-[α,β-methylene] diphosphoric acid, adenosine-5'[β,γ-methylene] triphosphate tetralithium salt, adenosine-5'-[β,γ-methylene] triphosphate tetralithium salt, adenosine-5'-monophosphoramidate sodium salt, adenosine-3'-monophosphoric acid, adeno-sine-3'-(+2)-monophosphoric acid monohydrate, adenosine-5'-monophosphoric acid monohydrate, adenosine-3'-phosphate-5'-phosphosulfate tetralithium salt tetrahydrate, adenosine-5'-[β-thio] di-phosphate trilithium salt, adenosine-5'-[α-thio] monophosphate dilithium salt, adenosine-5'-[γ-thio] triphosphate tetralithium salt, adenosine-5'-triphosphate, adenosine-5'-triphosphate bis (TRIS) salt dihydrate, adenosine-5'-triphosphate dipotassium salt dihydrate, adenosine-5'-triphosphate disodium salt hydrate, adenosine-5'-triphosphate magnesium salt hydrate, and adenosine-5'-triphosphate $P^3$-[1-(2-nitrophenyl) ethylester] disodium salt.

16. The composition of claim 12, wherein the adenosine compound is present at an amount ranging from about 1 to about 50 wt %, based on the total dry weight of the composition.

17. The composition of claim 12, wherein the composition further comprises a glucan.

18. The composition of claim 12, wherein the glucan is isolated from a yeast species selected from the group consisting of Candida, Saccharomyces, and Cryptococcus.

19. The composition of claim 17, wherein the glucan is selected from the group consisting of β-1,3-glucan, β-1,3-polyglucose, β-1,3-glucan glucopyranose, and β-1,3-D-polyglucose derivatives.

20. The composition of claim 17, wherein the glucan is present in an amount ranging from about 5 to about 99 wt %, based on the dry weight of the composition.

21. A composition for treating cancer comprising:
   (a) a first mixture of at least one compound selected from the group of alpha-alanine, an adenosine compound, a ribose compound, ascorbic acid, nicotinic acid, and a glucan;
   (b) a second mixture of at least one compound selected from the group of alpha-alanine, an adenosine compound, a ribose compound, ascorbic acid, nicotinic acid, and a glucan;

wherein the first mixture and the second mixture together contain about 8 to 15 wt % alpha-alanine, about 8 to 20 wt % of an adenosine compound, about 35 to 50 wt % of a ribose compound, about 15 to 28 wt % ascorbic acid, and about 6 to 15 wt % nicotinic acid; and wherein the first mixture and the second mixture are located in separate containers and are combinable to form a composition consisting essentially of alpha-alanine, an adenosine compound, a ribose compound, ascorbic acid, and nicotinic acid.

22. The composition of claim 1, wherein the first mixture comprises ascorbic acid and the ribose compound, and the second mixture comprises alpha-alanine, the adensoine compound, and nicotinic acid.

23. The composition of claim 21, wherein the alanine is D,L-alanine.

24. The composition of claim 22, wherein the second mixture mixture further comprises a glucan.

25. The composition of claim 24, wherein the glucan is selected from the group consisting of β-1,3-glucan, β-1,3-polyglucose, β-1,3-glucan glucopyranose, and β-1,3-D-polyglucose derivatives.

26. The composition of claim 24, wherein the glucan is present in an amount ranging from about 5 to about 99 wt %, based on the total dry weight of the composition.

27. The composition of claim 23, wherein the adenosine compound is present at an amount ranging from about 1 to about 50 wt %, based on the total dry weight of the composition.

28. The composition of claim 24, wherein the glucan is isolated from a yeast species selected from the group consisting of Candida, Saccharomyces, and Cryptococcus.

* * * * *

UNITED STATES PATENT AND TRADEMARK OFFICE
CERTIFICATE OF CORRECTION

PATENT NO. : 6,255,291 B1
DATED : July 3, 2001
INVENTOR(S) : Germano

It is certified that error appears in the above-identified patent and that said Letters Patent is hereby corrected as shown below:

Column 12,
Line 27, delete "adenosine-5'[β,γ-methylene]" and replace with -- adenosine-5'[α,β-methylene] --
Line 49, delete "12" and replace with -- 17 --

Column 13,
Line 11, delete "1" and replace with -- 23 --

Signed and Sealed this

Ninth Day of July, 2002

*Attest:*

*Attesting Officer*

JAMES E. ROGAN
*Director of the United States Patent and Trademark Office*